US008633240B2

(12) United States Patent
Harper et al.

(10) Patent No.: US 8,633,240 B2
(45) Date of Patent: Jan. 21, 2014

(54) PACLITAXEL TRIHYDRATES AND METHODS OF MAKING THEREOF

(75) Inventors: James K. Harper, Chuluota, FL (US); David M. Grant, Salt Lake City, UT (US)

(73) Assignee: The University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 13/486,229

(22) Filed: Jun. 1, 2012

(65) Prior Publication Data

US 2013/0324746 A1  Dec. 5, 2013

(51) Int. Cl.
C07D 305/00 (2006.01)
A61K 31/335 (2006.01)

(52) U.S. Cl.
USPC .......................................... 514/449; 549/510

(58) Field of Classification Search
USPC .......................................... 549/510; 514/449
See application file for complete search history.

(56) References Cited

U.S. PATENT DOCUMENTS

| | | | |
|---|---|---|---|
| 6,002,022 A * | 12/1999 | Authelin et al. | ............ 549/510 |
| 6,838,569 B2 | 1/2005 | Sharma et al. | |
| 7,332,617 B2 | 2/2008 | Li et al. | |
| 2004/0116720 A1 | 6/2004 | Sharma et al. | |
| 2007/0142457 A1 | 6/2007 | Pontiroli et al. | |

OTHER PUBLICATIONS

Heider, Elizabeth M. Phys. Chem. Chem. Phys., 2007, 9, 6083-6097.*
Mastropaolo et al.; *Crystal and molecular structure of paclitaxel (taxol)*; (Apr. 17, 1995); Proc. Natl. Acad. Sci. USA vol. 92, pp. 6920-6924, Jul. 1995.
Gu, Z. et al.; *Hydrogen Bonding of Carboxyl Groups in Solid-State Amino Acids and Peptides: Comparison of Carbon Chemical Shielding, Infrared Frequencies, and Structures*; J. Am. Chem. Soc. 1994, 116, pp. 6368-6372.
Ando, S. et al.; *Intermolecular Hydrogen-Bonding Effect on $^{13}C$ NMR Chemical Shifts of Glycine Residue Carbonyl Carbons of Peptides in the Solid State*; J. Am. Chem. Soc. 1988, 110, pp. 3380-3386.
Asakawa, N. et al.; *Hydrogen-Bonding Effect on $^{13}C$ NMR Chemical Shifts of L-Alanine Residue Carbonyl Carbons of Peptides in the Solid State* J. Am. Chem. Soc. 1992, 114, pp. 3261-3265.
Harper, J. K. et al.; *Solid-State $^{13}C$ Chemical Shift Tensors in Terpenes. 2. NMR Characterization of Distinct Molecules in the Asymmetric Unit and Steric Influences on Shift in Parthenolide*; J. Am. Chem. Soc. 1999, 121, pp. 6488-6496.

* cited by examiner

*Primary Examiner* — Noble Jarrell
*Assistant Examiner* — Laura Daniel
(74) *Attorney, Agent, or Firm* — Workman Nydegger

(57) ABSTRACT

Novel paclitaxel trihydrates. The paclitaxel trihydrates described herein are obtained by recrystallizing paclitaxel from a water/alcohol solution. Such recrystallization is known in the art to yield the one previously known paclitaxel crystalline trihydrate polymorph. Formation of the novel paclitaxel trihydrates described herein is induced by subjecting paclitaxel trihydrate crystals to an elevated pressure. As evidenced by NMR spectra, the novel paclitaxel trihydrates described herein have three-dimensional structures and/or water coordination geometry structures that are distinct from any previously known paclitaxel trihydrate.

21 Claims, 2 Drawing Sheets

PACLITAXEL TRIHYDRATES AND METHODS OF MAKING THEREOF

BACKGROUND

Since its discovery in 1971, paclitaxel (sold under the trade name Taxol®) (Formula 1) has become a powerful and widely used anticancer agent. Its unique

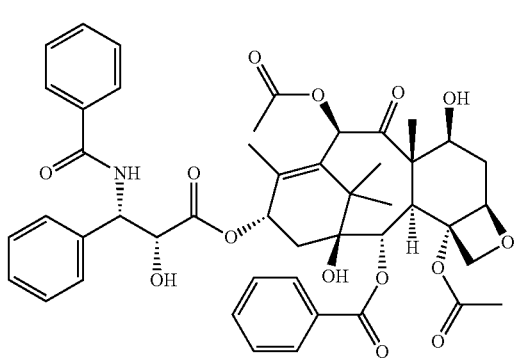

Formula 1 bioactivity promotes the assembly and stabilization of intracellular structures called microtubules. Microtubules are dynamic structures that are constantly being broken down and reformed within living cells. A notable structure involving microtubules is the mitotic spindle used by eukaryotic cells to segregate their chromosomes during cell division. The formation and subsequent degradation of the mitotic spindle is critical to the normal progression of mitosis. In the presence of paclitaxel, however, the stabilized microtubules cannot retract after chromosomal separation and cellular mitosis is terminated.

Paclitaxel successfully treats a number of cancers, including breast, ovarian and lung carcinomas. Additionally, paclitaxel has demonstrated efficacy in treating cancers resistant to other therapies, has been used to inhibit smooth muscle cell proliferation and migration for treatment of restinosis, and further applications of paclitaxel are presently under investigation. Enormous clinical success has made paclitaxel the focus of many studies.

Paclitaxel is known to occur in at least two crystalline forms: an anhydrate and a trihydrate. The occurrence of different crystalline forms (i.e., polymorphism) is a property of some molecules and molecular complexes. A single molecule, or a salt complex, may give rise to a variety of solids having distinct physical properties like melting point, X-ray diffraction pattern, infrared absorption fingerprint and various NMR spectra. The differences in the physical properties of different crystalline forms result from the orientation and intermolecular interactions of adjacent molecules (complexes) in the bulk solid. Accordingly, polymorphs are distinct solids sharing the same molecular formula yet having distinct advantageous and/or disadvantageous physical properties compared to other forms in the polymorph family. These properties can be influenced by controlling the conditions under which the solid form of a material is obtained.

Purified, anhydrous paclitaxel has been found to undergo degradation, even under controlled storage conditions. However, it has been found that paclitaxel trihydrate is considerably more stable than the anhydrate, which allows the trihydrate to retain its anti-cancer properties for longer compared to the anhydrate. Likewise, paclitaxel trihydrate may be more soluble than the anhydrate, which may lead to better drug delivery.

U.S. Pat. No. 6,002,022 to Authelin et al. describes a method for making the only known paclitaxel trihydrate form. The trihydrate described in the Authelin patent has a stability that is markedly superior to that of the anhydrous product. According to Authelin et al., paclitaxel trihydrate is obtained by recrystallization of paclitaxel from a mixture of water and an aliphatic alcohol containing up to three carbon atoms, specifically methanol. The water/alcohol weight ratio used in this process is between 3/1 to 1/3. The crystals, thus obtained, are dried at about 40° C. under reduced pressure. A nuclear magnetic resonance ("NMR") spectrum of the paclitaxel trihydrate crystalline polymorph described in Authelin et al. is illustrated herein in FIG. 1 as Taxol trihydrate I. Peak assignments associated with Taxol trihydrate I are listed in Table 5 in the column labeled Phase I $\delta^{13}C$.

The discovery of new forms of a pharmaceutically useful compound provides an opportunity, to improve the performance characteristics of a pharmaceutical product. It enlarges the repertoire of materials that a formulation scientist has available for designing, for example, a pharmaceutical dosage form of a drug with a targeted release profile or other desired characteristic. Additional polymorphic forms may further help in determination of polymorphic content of a batch of an active pharmaceutical ingredient, for example, by providing a useful reference standard for XRD instruments.

BRIEF SUMMARY

The present disclosure relates to novel paclitaxel trihydrates. The paclitaxel trihydrates described herein are obtained by recrystallizing paclitaxel from a water/alcohol solution. Such recrystallization is known in the art to yield the one previously known paclitaxel crystalline trihydrate polymorph. Formation of the novel paclitaxel trihydrates described herein is induced by subjecting paclitaxel trihydrate crystals to an elevated pressure to transform the polymorphic structures. As evidenced by NMR spectra, the novel paclitaxel trihydrates described herein have three-dimensional structures and/or water coordination geometry structures that are distinct from the previously known paclitaxel trihydrate. It is expected that the novel crystalline paclitaxel trihydrates described herein may be more stable than the anhydrate form and may be more stable than the previously known trihydrate. Likewise, it is hypothesized that the novel paclitaxel trihydrates described herein may be more soluble than the anhydrate and may be more soluble in comparable solvents than the previously known trihydrate, which may lead to better drug delivery.

In one embodiment, isolated crystalline paclitaxel trihydrates are described. The isolated crystalline paclitaxel trihydrates are characterized by having one of a $^{13}C$ NMR spectrum illustrated at Taxol trihydrate II in FIG. 1 or a $^{13}C$ NMR spectrum illustrated at Taxol Trihydrate III (TA05) in FIG. 1.

In one embodiment a first novel crystalline paclitaxel trihydrate (i.e., Trihydrate II or Phase II) is described. The first novel crystalline paclitaxel trihydrate is characterized by having $\delta$ $^{13}C$/ppm chemical shifts comprising:

| Trihydrate II | |
|---|---|
| Carbon # | Phase II δ $^{13}$C |
| 4 | 81.0 |
| 5 | 84.9 |
| 9 | 203.6, 207.4 |
| 17 | 24.0 |

In one aspect, the first novel crystalline paclitaxel trihydrate is further characterized by having δ $^{13}$C/ppm chemical shifts comprising:

| Trihydrate II | |
|---|---|
| Carbon # | Phase II δ $^{13}$C |
| 1 | 79.3 |
| 2 | 75.2 |
| 3 | 46.6, 47.2 |
| 6 | 38.1, 39.8 |
| 7 | 73.7, 74.3 |
| 8 | 58.6, 59.1 |
| 10 | 75.3, 77.1 |
| 11 | 132.9, 134.1 |
| 12 | 141.8, 142.6 |
| 13 | 71.9 |
| 14 | 34.6, 35.9 |
| 15 | 43.4, 44.0 |
| 16 | 26.1, 27.3 |
| 18 | 13.8, 14.0 |
| 19 | 11.7, 12.3 |
| 20 | 76.9 |
| 21 | 167.0, 167.8 |
| 22 | 127.4 |
| 28 | 171.5 |
| 29 | 23.8 |
| 30 | 173.2, 175.6 |
| 31 | 22.2 |

In another aspect, the first novel crystalline paclitaxel trihydrate is further characterized as having a $^{13}$C NMR spectrum illustrated as Taxol trihydrate II in FIG. 1.

In another embodiment, a second novel crystalline paclitaxel trihydrate (i.e., Trihydrate III or Phase III) is described. The second novel crystalline paclitaxel trihydrate is characterized by having δ $^{13}$C/ppm chemical shifts comprising:

| Trihydrate III | |
|---|---|
| Carbon # | Phase III δ $^{13}$C |
| 4 | 80.5, 81.6 |
| 5 | 84.8, 85.4 |
| 9 | 201.9, 204.1 |
| 17 | 21.9, 24.4 |

In one aspect, a second novel crystalline paclitaxel trihydrate is further characterized by having δ $^{13}$C/ppm chemical shifts comprising:

| Trihydrate III | |
|---|---|
| Carbon # | Phase III δ $^{13}$C |
| 1 | 79.0 |
| 2 | 76.3 |

| Trihydrate III | |
|---|---|
| Carbon # | Phase III δ $^{13}$C |
| 3 | 47.2, 48.2 |
| 6 | 38.4, 39.3 |
| 7 | 74.5 |
| 8 | 58.1, 58.5 |
| 10 | 76.4 |
| 11 | 133.3, 134.0 |
| 12 | 140.6, 141.0 |
| 13 | 71.6 |
| 14 | 36.4, 36.6 |
| 15 | 43.2, 43.7 |
| 16 | 26.1, 26.7 |
| 18 | 13.5, 14.5 |
| 19 | 11.6, 12.0 |
| 20 | 77.0 |
| 21 | 169.5, 169.9 |
| 22 | 128.8, 129.0 |
| 28 | 169.9 |
| 29 | 21.6 |
| 30 | 171.1, 171.9 |
| 31 | 22.5, 22.9 |

In another aspect, the second novel crystalline paclitaxel trihydrate is further characterized as having a $^{13}$C NMR spectrum illustrated as Taxol Trihydrate III (TA05) in FIG. 1.

In yet another embodiment, a pharmaceutical composition containing a pharmaceutically effective amount of a crystalline paclitaxel trihydrate is described. The crystalline paclitaxel trihydrate is characterized by having at least one of a $^{13}$C NMR spectrum illustrated at Taxol trihydrate II in FIG. 1 or a $^{13}$C NMR spectrum illustrated at Taxol Trihydrate III (TA05) in FIG. 1.

Pharmaceutical compositions may be prepared as medicaments for administration by any suitable route of administration. Suitable routes of administration may include, but are not limited to, oral, parenteral, rectal, transdermal, bucal, or nasal. For example, paclitaxel is typically administered intravenously. For administration, paclitaxel is typically dissolved in a nonaqueous solvent (e.g., ethanol) with an excipient (e.g., polyoxyethylated castor oil (Cremophor® EL)). The nonaqueous solution is intended for dilution with a suitable parenteral fluid (e.g., sterile, isotonic saline) prior to intravenous infusion.

In one aspect, a first novel crystalline paclitaxel trihydrate of the pharmaceutical composition is characterized by having δ $^{13}$C/ppm chemical shifts comprising:

| Trihydrate II | |
|---|---|
| Carbon # | Phase II δ $^{13}$C |
| 1 | 79.3 |
| 2 | 75.2 |
| 3 | 46.6, 47.2 |
| 6 | 38.1, 39.8 |
| 7 | 73.7, 74.3 |
| 8 | 58.6, 59.1 |
| 10 | 75.3, 77.1 |
| 11 | 132.9, 134.1 |
| 12 | 141.8, 142.6 |
| 13 | 71.9 |
| 14 | 34.6, 35.9 |
| 15 | 43.4, 44.0 |
| 16 | 26.1, 27.3 |
| 18 | 13.8, 14.0 |
| 19 | 11.7, 12.3 |
| 20 | 76.9 |

-continued

Trihydrate II

| Carbon # | Phase II δ $^{13}$C |
|---|---|
| 21 | 167.0, 167.8 |
| 22 | 127.4 |
| 28 | 171.5 |
| 29 | 23.8 |
| 30 | 173.2, 175.6 |
| 31 | 22.2 |

In one aspect, a second novel crystalline paclitaxel trihydrate of the pharmaceutical composition is further characterized by having δ $^{13}$C/ppm chemical shifts comprising:

Trihydrate III

| Carbon # | Phase III δ $^{13}$C |
|---|---|
| 1 | 79.0 |
| 2 | 76.3 |
| 3 | 47.2, 48.2 |
| 6 | 38.4, 39.3 |
| 7 | 74.5 |
| 8 | 58.1, 58.5 |
| 10 | 76.4 |
| 11 | 133.3, 134.0 |
| 12 | 140.6, 141.0 |
| 13 | 71.6 |
| 14 | 36.4, 36.6 |
| 15 | 43.2, 43.7 |
| 16 | 26.1, 26.7 |
| 18 | 13.5, 14.5 |
| 19 | 11.6, 12.0 |
| 20 | 77.0 |
| 21 | 169.5, 169.9 |
| 22 | 128.8, 129.0 |
| 28 | 169.9 |
| 29 | 21.6 |
| 30 | 171.1, 171.9 |
| 31 | 22.5, 22.9 |

In one embodiment, a method for preparing a paclitaxel trihydrate is described. The method includes (1) preparing a crystalline paclitaxel trihydrate phase characterized as having a $^{13}$C NMR spectrum illustrated at Taxol trihydrate I in FIG. 1, and (2) inducing a phase change to yield a new paclitaxel trihydrate phase (i.e., Phase II), wherein the new paclitaxel trihydrate phase is characterized by having δ $^{13}$C/ppm chemical shifts comprising:

| Carbon # | Phase II δ $^{13}$C |
|---|---|
| 4 | 81.0 |
| 5 | 84.9 |
| 9 | 203.6, 207.4 |
| 17 | 24.0 |

In one embodiment, the crystalline paclitaxel trihydrate phase characterized as having a $^{13}$C NMR spectrum illustrated at Taxol trihydrate I in FIG. 1 (i.e., Phase I) can be used to make at least two new paclitaxel trihydrate phases described herein (i.e., Phase II and Phase III). In one embodiment, Phase II can be made by preparing Phase I and then inducing a first phase change to yield Phase II. Likewise, Phase III can be prepared by preparing Phase II and then inducing a second phase change to yield Phase III.

In one embodiment, inducing a phase change from Phase I to Phase II or a from Phase II to Phase III includes subjecting Phase I or Phase II to an elevated pressure (i.e., an elevated compressive force) under ambient temperature and humidity conditions for a time sufficient to induce the first and/or the second phase change. In one embodiment, the elevated pressure is in a range from about 0.3 MPa to about 4 MPa, about 0.5 MPa to about 3 MPa, about 0.8 MPa to about 2.5 MPa, or, preferably, about 1 MPa to about 2.2 MPa. One will appreciate that, within reason, the higher the pressure, the more rapid the conversion from Phase I to Phase II or from Phase II to Phase III.

In one embodiment, such an elevated pressure can be induced by spinning the paclitaxel material in a solid-state NMR probe centrifuge at a speed of at least 800-4000 Hz. Spinning the paclitaxel material at a speed of about 800-4000 Hz (e.g., about 3000 Hz) subjects the material to an elevated pressure of about 1 MPa to about 2.2 MPa (i.e., ~10-22 Atm.), respectively, at the wall of the sample container. Spinning at 860 Hz induced the change from Phase I to Phase II in approximately 3 days, while 4000 Hz spinning completed the phase transformation in less than 1 day. One will appreciate that the more rapidly the sample is spun (the sample is subjected to elevated pressures (i.e., elevated compressive forces) at greater speeds), the more rapid the conversion from Phase I to Phase II or from Phase II to Phase III.

In one embodiment, inducing the phase change to yield Phase II includes subjecting Phase I to an elevated pressure for a time sufficient to induce the first phase change. This elevated pressure may be generated, for example, by spinning the sample between 800-4000 Hz in a solid-state NMR rotor.

Paclitaxel trihydrate Phase II is characterized by having δ $^{13}$C/ppm chemical shifts comprising:

| Carbon # | Phase II δ $^{13}$C |
|---|---|
| 4 | 81.0 |
| 5 | 84.9 |
| 9 | 203.6, 207.4 |
| 17 | 24.0 |

In one embodiment, paclitaxel trihydrate Phase II is further characterized as having a $^{13}$C NMR spectrum illustrated as Taxol trihydrate II in FIG. 1.

In one embodiment, the method further includes inducing a second phase change following the first phase change to yield paclitaxel trihydrate Phase III. Paclitaxel trihydrate Phase III is characterized by having δ $^{13}$C/ppm chemical shifts comprising:

| Carbon # | Phase III δ $^{13}$C |
|---|---|
| 4 | 80.5, 81.6 |
| 5 | 84.8, 85.4 |
| 9 | 201.9, 204.1 |
| 17 | 21.9, 24.4 |

In one embodiment, Phase III is further characterized as having a $^{13}$C NMR spectrum illustrated at Taxol trihydrate III (TA05) in FIG. 1.

In one embodiment, inducing the second phase change to yield Phase III includes subjecting Phase II to an elevated pressure under ambient temperature and humidity conditions for a time sufficient to induce the second phase change. In one embodiment, subjecting Phase II to an elevated pressure includes spinning Phase II in a solid-state NMR spinning module (e.g., a probe centrifuge) at a rate of rotation of at least 800-4000 Hz (e.g., 3000 Hz) for a time sufficient to yield Phase III.

These and other objects and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which.

DETAILED DESCRIPTION

Figure 1:
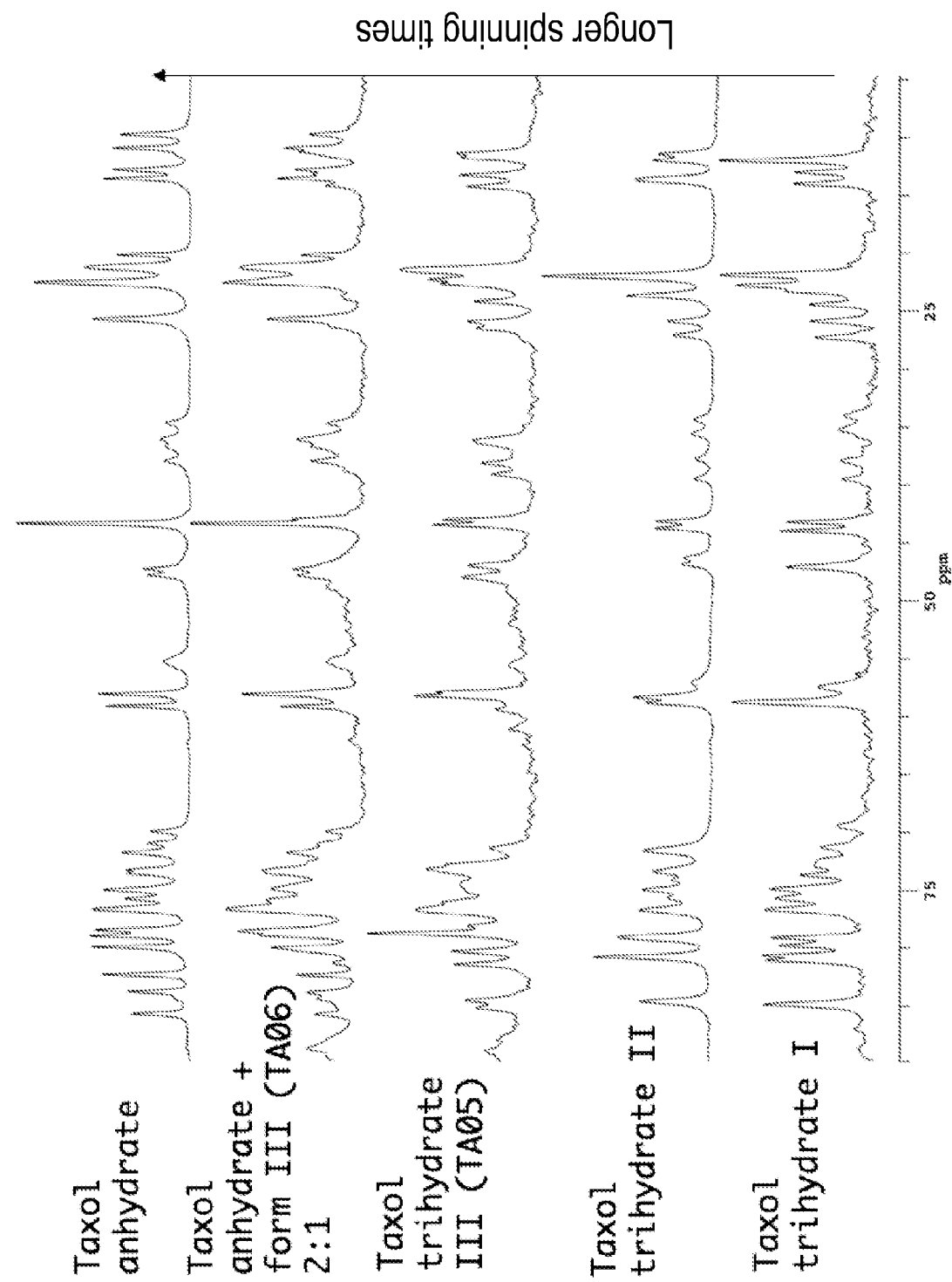
FIG. 1 illustrates spectra ($^{13}$C) of the aliphatic region of paclitaxel illustrating the phase changes that occur upon spinning the sample at 4 kHz. Taxol trihydrate I is the NMR spectrum for the trihydrate described in U.S. Pat. No. 6,002,022 to Authelin et al.; Taxol anhydrate is the NMR spectrum for the anhydrous form of taxol; Taxol Trihydrate II (i.e., Phase II) and Taxol trihydrate III (TA05) (i.e., Phase III) are the NMR spectra for the novel taxol trihydrates described herein; and the spectrum labeled Taxol anhydrate+form III (TA06) is believed to be for a mixed phase that includes anhydrate and phase III.

The present disclosure relates to novel paclitaxel trihydrates. The paclitaxel trihydrates described herein are obtained by recrystallizing paclitaxel from a water/alcohol solution. Such recrystallization is known in the art to yield the one previously known paclitaxel crystalline trihydrate polymorph. Formation of the novel paclitaxel trihydrates described herein is induced by subjecting paclitaxel trihydrate crystals to an elevated pressure (e.g., from rapid sample spinning in a solid-state NMR probe module). As evidenced by NMR spectra, the novel paclitaxel trihydrates described herein have three-dimensional structures and/or water coordination geometry structures that are distinct from the previously known paclitaxel trihydrate. It is expected that the novel crystalline paclitaxel trihydrates described herein will be more stable than the anhydrate form and may be more stable that the previously known trihydrate. Likewise, it is hypothesized that the novel paclitaxel trihydrates described herein may be more soluble than the anhydrate and may be more soluble in comparable solvent than the previously known trihydrate, which may lead to better drug delivery.

Preparation of New Two Phases of Paclitaxel in the Solid-State.

Two new phases of paclitaxel, both trihydrates, were prepared by subjecting a first, previously reported, paclitaxel trihydrate to high speed spinning (e.g., about 3 kHz) in a solid-state NMR probe to induce a phase change. Phase changes were monitored by periodically acquiring 1D $^{13}$C spectra and noting differences in chemical shifts. For this process, the initial paclitaxel trihydrate phase (denoted here as Phase I) was prepared by dissolving any other phase of paclitaxel in methanol (reagent grade) then adding water (HPLC grade) drop-wise with stirring until paclitaxel began to precipitate out of solution. After no new paclitaxel precipitation was observed, an additional 1-2 mL of water was added and the solution stirred to ensure homogeneity. This slurry was placed on a hot plate and heated until all solid paclitaxel dissolved and the resulting clear solution was then covered by a watch glass and allowed to sit at room temperature. Paclitaxel crystals formed from this solution in approximately 1 hour. This precipitate was allowed to stand at room temperature for approximately 2 weeks until all liquid had evaporated leaving a white solid referred to here as Phase I. Elemental analysis of this solid found an elemental composition consistent with paclitaxel trihydrate as summarized in Table 1. This paclitaxel trihydrate, which is the starting material for producing the novel paclitaxel trihydrates described herein, is the same trihydrate that has been described in U.S. Pat. No. 6,002,022 to Authelin et al. as well as a number of other sources.

TABLE 1

Elemental analysis for paclitaxel Phase I.

| Element | Theory for paclitaxel • 3H$_2$O (%) | Experimentally found (%) | % error |
|---|---|---|---|
| C | 62.17 | 62.57 ± 0.3 | 0.40 |
| O | 29.96 | 29.81 ± 0.3 | −0.15 |
| N | 1.54 | 1.48 ± 0.3 | −0.06 |
| H | 6.33 | 6.20 ± 0.3 | −0.13 |

Other levels of hydration (i.e. paclitaxel.1 H$_2$O and paclitaxel.2 H$_2$O) gave significantly worse fits to experimental data, eliminating them as possible new phases. An X-ray diffraction powder pattern of Phase I was acquired at the Argonne synchrotron and was found to match the powder pattern reported in U.S. Pat. No. 6,002,022. Spinning the trihydrate at 4.0 kHz for several days in a solid-state NMR probe showed a series of three phase changes occurring with four pure phases observed and one mixed phase. These phases are denoted as Phase I, Phase II, Phase III and the anhydrate. $^{13}$C spectra for the aliphatic carbons of Phase I, Phase II, Phase III and the anhydrate are shown in FIG. 1. The anhydrate is known from prior work (see, Heider, E. M. et al. *Phys. Chem. Chem. Phys.* 2007, 9, 1 the entirety of which is incorporated herein by reference) and it can be recognized that the mixed phase consists of this anhydrate and Phase III. The resulting spectra, including the anhydrate, are shown in FIG. 1.

The NMR spectra illustrated in FIG. 1 clearly show that the structures of Taxol trihydrate II (i.e., Phase II) and Taxol trihydrate III (TA05) (i.e., Phase III) are different from either the structure of Taxol trihydrate I or Taxol anhydrate. The distinct nature of the structures of Taxol trihydrate II and Taxol trihydrate III (TA05) is demonstrated by, for example, the appearance and disappearance of peaks in the NMR spectra between about 10 ppm to 30 ppm.

Figure 2:
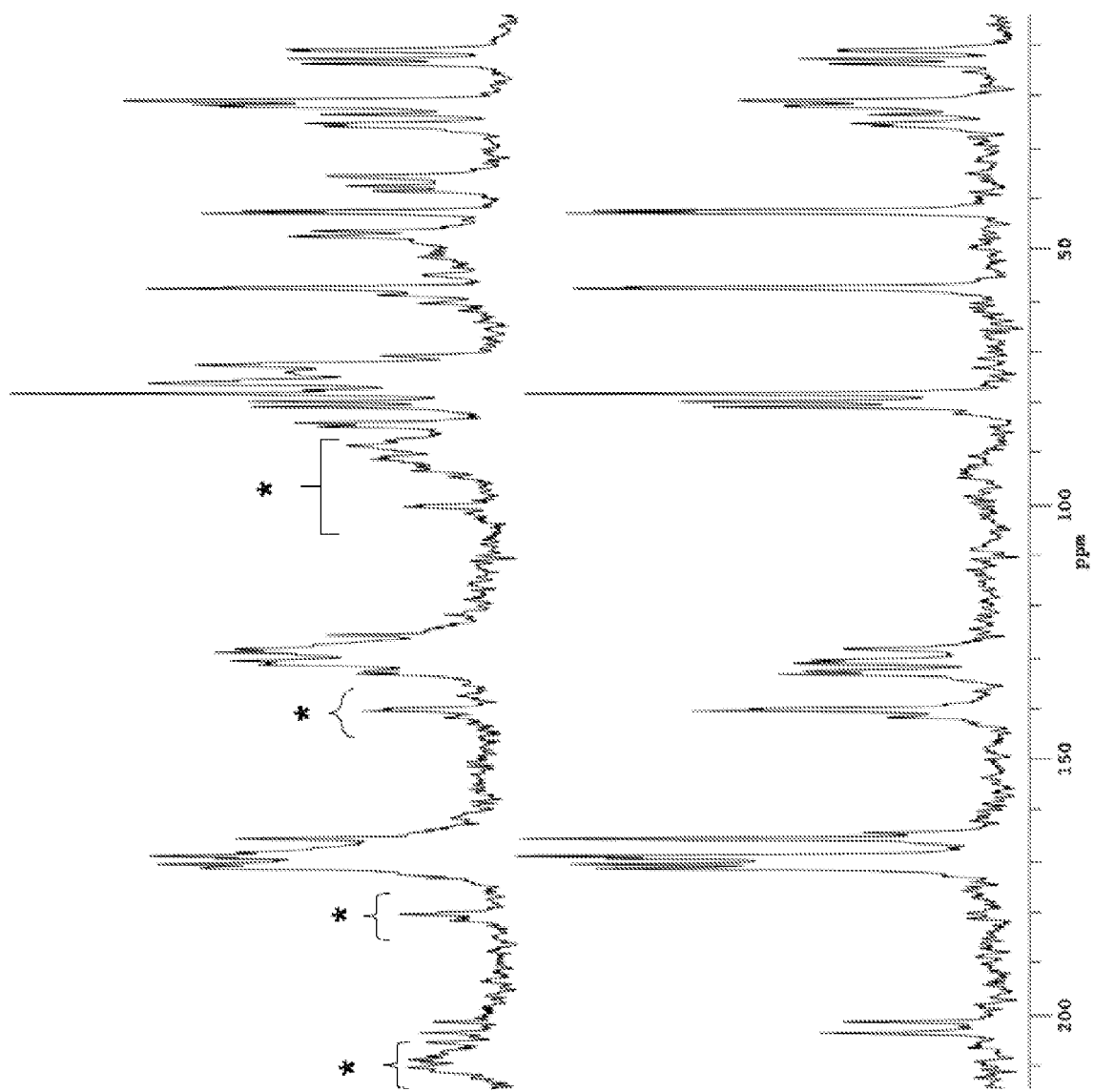
FIG. 2 illustrates spectra ($^{13}$C) for paclitaxel Phase III. The upper spectrum includes all peaks and has some artifacts, as indicated by *, resulting from sample spinning speed. The lower spectrum suppresses these artifacts and illustrates chemical shifts only for non-protonated peaks carbons and the methyls (i.e. all peaks below 35 ppm).

A full spectrum of Phase III is shown in FIG. 2 with the lower spectrum showing only non-protonated peaks and methyls.

To confirm the composition of Phases II and III and the mixed phase, elemental analyses were performed on Phases II and III and the mixed phase to determine the levels of hydration (Tables 2-4).

TABLE 2

Elemental analysis of paclitaxel Phase II.

| Element | Theory for paclitaxel • 3H$_2$O (%) | Experimentally found (%) | Error (%) |
|---|---|---|---|
| C | 62.17 | 62.13 ± 0.3 | −0.04 |
| O | 29.96 | Analysis not performed | — |
| N | 1.54 | 1.46 ± 0.3 | −0.08 |
| H | 6.33 | 6.37 ± 0.3 | 0.04 |

TABLE 3

Elemental analysis for paclitaxel Phase III.

| Element | Theory for paclitaxel • 3H$_2$O (%) | Experimentally found (%) | % error |
|---|---|---|---|
| C | 62.17 | 62.73 ± 0.3 | 0.56 |
| O | 29.96 | 29.11 ± 0.3 | −0.85 |
| N | 1.54 | 1.59 ± 0.3 | 0.05 |
| H | 6.33 | 6.27 ± 0.3 | −0.06 |

TABLE 4

Elemental analysis for the 1:2 mix of paclitaxel Phase III:anhydrate.

| Element | Theory for 1:2 mix of paclitaxel Phase III:anhydrate (%) | Experimentally found (%) | Error (%) |
|---|---|---|---|
| C | 64.79 | 64.13 ± 0.3 | −0.66 |
| O | 27.52 | 27.19 ± 0.3 | 0.39 |
| N | 1.61 | 1.61 ± 0.3 | 0.00 |
| H | 6.13 | 6.20 ± 0.3 | 0.07 |

The NMR data, when combined with the elemental analysis for Phases II and III, indicate that these phases are new trihydrates and that the mixed phase is a 2:1 mix of paclitaxel anhydrate:paclitaxel trihydrate (Phase III).

One risk inherent to the elemental analyses is that rehydration could occur during analysis. For example, Phase II may have appeared to be a monohydrate and the act of preparing the sample in a humid environment could cause a phase change back to the trihydrate (i.e., Phase I). Precautions were taken to prevent rehydration that involved sealing the sample in a glass vial immediately upon formation of the desired phase. However, to more fully evaluate the risk of rehydration, a sample of the mixed phase (Table 4) was sent for elemental. This phase is predicted to consist of roughly 66% anhydrate and 33% trihydrate based on comparison with the NMR spectra of the pure anhydrate and Phase III. If rehydration occurred during sample preparation, the elemental analysis should match the data listed in Table 1. If no rehydration occurs during analysis, this phase should have the elemental compositions shown in the second column of Table 4. The close match between the predicted and experimental compositions in Table 4 demonstrates that rehydration did not occur during the elemental analyses.

The two new paclitaxel trihydrate phase designations of Phase II and Phase III are intended to indicate the order in which the phases occur (i.e., Phase I is found first upon air drying the recrystallized solid with Phase II arising after some spinning, Phase III arising after additional spinning, etc.). The $\delta^{13}$C shifts of all phases and tentative shift assignments are given below in Table 5. All shift assignments are made by a comparison to prior assignments performed by the inventors earlier in paclitaxel anhydrate (Heider, E. M. et al. Phys. Chem. Chem. Phys. 2007, 9, 1). Numbering of molecular positions is shown below in Formula 2. All spectra were externally referenced to the methyl peak of hexamethyl benzene at 17.35 ppm. No internal referencing is typically used in solid-state NMR and none was used here.

Formula 2

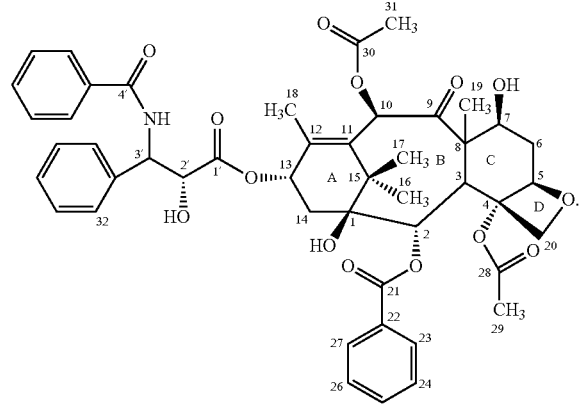

Structure of paclitaxel and the numbering used herein.

TABLE 5

The $\delta^{13}$C shifts (ppm) for paclitaxel trihydrate Phases I, II and III.[a]

| Carbon # | Phase I $\delta^{13}$C | Phase II $\delta^{13}$C | Phase III $\delta^{13}$C |
|---|---|---|---|
| 1 | 79.2, 80.0 | 79.3 | 79.0 |
| 2 | 75.3 | 75.2 | 76.3 |
| 3 | 47.1, 47.2 | 46.6, 47.2 | 47.2, 48.2 |
| 4 | 80.8, 81.1 | 81.0 | 80.5, 81.6 |
| 5 | 84.9 | 84.9 | 84.8, 85.4 |
| 6 | 38.1, 39.4 | 38.1, 39.8 | 38.4, 39.3 |
| 7 | 76.7 | 73.7, 74.3 | 74.5 |
| 8 | 58.8, 59.0 | 58.6, 59.1 | 58.1, 58.5 |
| 9 | 203.5, 209.4 | 203.6, 207.4 | 201.9, 204.1 |
| 10 | 74.7, 75.5 | 75.3, 77.1 | 76.4 |
| 11 | 132.2, 133.3 | 132.9, 134.1 | 133.3, 134.0 |
| 12 | 141.4 | 141.8, 142.6 | 140.6, 141.0 |
| 13 | 71.2 | 71.9 | 71.6 |
| 14 | 34.0, 35.2 | 34.6, 35.9 | 36.4, 36.6 |
| 15 | 43.3, 44.1 | 43.4, 44.0 | 43.2, 43.7 |
| 16 | 25.6, 27.5 | 26.1, 27.3 | 26.1, 26.7 |
| 17 | 22.0, 22.9 | 24.0 | 21.9, 24.4 |
| 18 | 13.0, 14.2 | 13.8, 14.0 | 13.5, 14.5 |
| 19 | 11.9, 12.3 | 11.7, 12.3 | 11.6, 12.0 |
| 20 | 76.4 | 76.9 | 77.0 |
| 21 | 167.7 | 167.0, 167.8 | 169.5, 169.9 |
| 22 | 126.9 | 127.4 | 128.8, 129.0 |
| 28 | 170.5 | 171.5 | 169.9 |
| 29 | 23.7, 24.3 | 23.8 | 21.6 |
| 30 | 172.9, 174.6 | 173.2, 175.6 | 171.1, 171.9 |
| 31 | 21.8 | 22.2 | 22.5, 22.9 |
| 1' | 170.3, 170.5 | 170.1, 170.7 | 170.5, 170.7 |
| 2' | 72.9, 73.9 | 73.6, 76.0 | 73.0 |
| 3' | 58.8, 59.0 | 57.4 | 55.5 |
| 4' | Not observed | Not observed | 164.9, 166.1 |
| 3'-ipso | 141.9 | Not observed | 142.4 |
| 4'-ipso | 137.8 | 138.9 | 131.1, 131.8 |
| Aromatic CHs[b] | 128-130 | 125-131, 131.5, 133.3 | 126.2, 128.1, 130.1, 132.1, |

[a]all spectra referenced to the methyl peak of hexamethyl benzene at 17.35 ppm.
[b]Extensive overlap was observed for protonated aromatic carbons and no assignments were made. The shifts listed represent only the clearly resolved resonances.

A comparison of the spectra of the Phases II and III shows differences at many sites. This can be appreciated by visually inspecting FIG. 1. Some of these differences are notable because they reflect structural difference between the different phases. In particular it has been demonstrated that differences in shifts at C=O sites is strongly correlated with differences in hydrogen bonding with the higher frequency shifts indicating stronger hydrogen bonding at the C=O (see, e.g., Gu, Z. et al. *J. Am. Chem. Soc.* 1994, 116, 6368, Ando, S. et al. *J. Am. Chem. Soc.* 1988, 110, 3380, Asakawa, N. et al. *J. Am. Chem. Soc.* 1992, 114, 3261 the entireties of which are incorporated herein by reference). Likewise, carbons bonded to an OH can vary with hydrogen bonding, but the direction of the shift change is less predictable in this case. Finally, steric effects near methyl groups are also reflected in the shift with lower frequencies indicating a more crowded environment near a $CH_3$ (see, e.g., Harper, J. K. et al. *J. Am. Chem. Soc.* 1999, 121, 6488 the entirety of which is incorporated herein by reference). With these variations in mind it is notable that the shifts at C4, C5, C9 and C17 differ as shown below. Note that all phases (i.e., Phases I, II and III) contain 2 geometrically distinct molecules in the unit cell, thus 2 shifts for each position are frequently observed.

TABLE 6

The $\delta^{13}C$ shifts (ppm) for selected sites in paclitaxel trihydrate Phases I, II and III.

| Site | Phase I | Phase II | Phase III |
| --- | --- | --- | --- |
| C4 | 80.8, 81.1 | 81.0 | 80.5, 81.6 |
| C5 | 84.9 | 84.9 | 84.8, 85.4 |
| C9 | 203.5, 209.4 | 203.6, 207.4 | 201.9, 204.1 |
| C17 | 22.0, 22.9 | 24.0 | 21.9, 24.4 |

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An isolated crystalline paclitaxel trihydrate characterized by having one of a $^{13}C$ NMR spectrum illustrated at Taxol trihydrate II in FIG. 1 or a $^{13}C$ NMR spectrum illustrated at Taxol Trihydrate III (TA05) in FIG. 1.

2. The isolated crystalline paclitaxel trihydrate of claim 1, wherein Taxol trihydrate II is further characterized by having $\delta$ $^{13}C$/ppm chemical shifts comprising:

| Carbon # | Phase II $\delta^{13}C$ |
| --- | --- |
| 4 | 81.0 |
| 5 | 84.9 |
| 9 | 203.6, 207.4 |
| 17 | 24.0 |

3. The isolated crystalline paclitaxel trihydrate of claim 2, wherein Taxol trihydrate II is further characterized by having $\delta$ $^{13}C$/ppm chemical shifts comprising:

| Carbon # | Phase II $\delta^{13}C$ |
| --- | --- |
| 1 | 79.3 |
| 2 | 75.2 |
| 3 | 46.6, 47.2 |
| 6 | 38.1, 39.8 |
| 7 | 73.7, 74.3 |
| 8 | 58.6, 59.1 |
| 10 | 75.3, 77.1 |
| 11 | 132.9, 134.1 |
| 12 | 141.8, 142.6 |
| 13 | 71.9 |
| 14 | 34.6, 35.9 |
| 15 | 43.4, 44.0 |
| 16 | 26.1, 27.3 |
| 18 | 13.8, 14.0 |
| 19 | 11.7, 12.3 |
| 20 | 76.9 |
| 21 | 167.0, 167.8 |
| 22 | 127.4 |
| 28 | 171.5 |
| 29 | 23.8 |
| 30 | 173.2, 175.6 |
| 31 | 22.2. |

4. The isolated crystalline paclitaxel trihydrate of claim 1, wherein Taxol Trihydrate III is further characterized by having $\delta$ $^{13}C$/ppm chemical shifts comprising:

| Carbon # | Phase III $\delta^{13}C$ |
| --- | --- |
| 4 | 80.5, 81.6 |
| 5 | 84.8, 85.4 |
| 9 | 201.9, 204.1 |
| 17 | 21.9, 24.4. |

5. The isolated crystalline paclitaxel trihydrate of claim 4, wherein Taxol Trihydrate III is further characterized by having $\delta$ $^{13}C$/ppm chemical shifts comprising:

| Carbon # | Phase III $\delta^{13}C$ |
| --- | --- |
| 1 | 79.0 |
| 2 | 76.3 |
| 3 | 47.2, 48.2 |
| 6 | 38.4, 39.3 |
| 7 | 74.5 |
| 8 | 58.1, 58.5 |
| 10 | 76.4 |
| 11 | 133.3, 134.0 |
| 12 | 140.6, 141.0 |
| 13 | 71.6 |
| 14 | 36.4, 36.6 |
| 15 | 43.2, 43.7 |
| 16 | 26.1, 26.7 |
| 18 | 13.5, 14.5 |
| 19 | 11.6, 12.0 |
| 20 | 77.0 |
| 21 | 169.5, 169.9 |
| 22 | 128.8, 129.0 |
| 28 | 169.9 |
| 29 | 21.6 |
| 30 | 171.1, 171.9 |
| 31 | 22.5, 22.9. |

6. The isolated crystalline paclitaxel trihydrate of claim 1, wherein Taxol Trihydrate II is further characterized by having $\delta$ $^{13}C$/ppm chemical shifts comprising:

| Carbon # | Phase II δ¹³C |
|---|---|
| 1 | 79.3 |
| 2 | 75.2 |
| 3 | 46.6, 47.2 |
| 4 | 81.0 |
| 5 | 84.9 |
| 6 | 38.1, 39.8 |
| 7 | 73.7, 74.3 |
| 8 | 58.6, 59.1 |
| 9 | 203.6, 207.4 |
| 10 | 75.3, 77.1 |
| 11 | 132.9, 134.1 |
| 12 | 141.8, 142.6 |
| 13 | 71.9 |
| 14 | 34.6, 35.9 |
| 15 | 43.4, 44.0 |
| 16 | 26.1, 27.3 |
| 17 | 24.0 |
| 18 | 13.8, 14.0 |
| 19 | 11.7, 12.3 |
| 20 | 76.9 |
| 21 | 167.0, 167.8 |
| 22 | 127.4 |
| 28 | 171.5 |
| 29 | 23.8 |
| 30 | 173.2, 175.6 |
| 31 | 22.2. |

7. The isolated crystalline paclitaxel trihydrate of claim 1, wherein Taxol Trihydrate III is further characterized by having δ ¹³C/ppm chemical shifts comprising:

| Carbon # | Phase III δ¹³C |
|---|---|
| 1 | 79.0 |
| 2 | 76.3 |
| 3 | 47.2, 48.2 |
| 4 | 80.5, 81.6 |
| 5 | 84.8, 85.4 |
| 6 | 38.4, 39.3 |
| 7 | 74.5 |
| 8 | 58.1, 58.5 |
| 9 | 201.9, 204.1 |
| 10 | 76.4 |
| 11 | 133.3, 134.0 |
| 12 | 140.6, 141.0 |
| 13 | 71.6 |
| 14 | 36.4, 36.6 |
| 15 | 43.2, 43.7 |
| 16 | 26.1, 26.7 |
| 17 | 21.9, 24.4 |
| 18 | 13.5, 14.5 |
| 19 | 11.6, 12.0 |
| 20 | 77.0 |
| 21 | 169.5, 169.9 |
| 22 | 128.8, 129.0 |
| 28 | 169.9 |
| 29 | 21.6 |
| 30 | 171.1, 171.9 |
| 31 | 22.5, 22.9. |

8. A pharmaceutical composition containing a pharmaceutically effective amount of a crystalline paclitaxel trihydrate, wherein the crystalline paclitaxel trihydrate is characterized by having at least one of a ¹³C NMR spectrum illustrated at Taxol trihydrate II in FIG. 1 or a ¹³C NMR spectrum illustrated at Taxol Trihydrate III (TA05) in FIG. 1.

9. The pharmaceutical composition of claim 8, wherein Taxol trihydrate II is further characterized by having δ ¹³C/ppm chemical shifts comprising:

| Carbon # | Phase II δ¹³C |
|---|---|
| 4 | 81.0 |
| 5 | 84.9 |
| 9 | 203.6, 207.4 |
| 17 | 24.0. |

10. The pharmaceutical composition of claim 9, wherein Taxol trihydrate II is further characterized by having δ ¹³C/ppm chemical shifts comprising:

| Carbon # | Phase II δ¹³C |
|---|---|
| 1 | 79.3 |
| 2 | 75.2 |
| 3 | 46.6, 47.2 |
| 6 | 38.1, 39.8 |
| 7 | 73.7, 74.3 |
| 8 | 58.6, 59.1 |
| 10 | 75.3, 77.1 |
| 11 | 132.9, 134.1 |
| 12 | 141.8, 142.6 |
| 13 | 71.9 |
| 14 | 34.6, 35.9 |
| 15 | 43.4, 44.0 |
| 16 | 26.1, 27.3 |
| 18 | 13.8, 14.0 |
| 19 | 11.7, 12.3 |
| 20 | 76.9 |
| 21 | 167.0, 167.8 |
| 22 | 127.4 |
| 28 | 171.5 |
| 29 | 23.8 |
| 30 | 173.2, 175.6 |
| 31 | 22.2. |

11. The pharmaceutical composition of claim 8, wherein Taxol trihydrate III is further characterized by having δ ¹³C/ppm chemical shifts comprising:

| Carbon # | Phase III δ¹³C |
|---|---|
| 4 | 80.5, 81.6 |
| 5 | 84.8, 85.4 |
| 9 | 201.9, 204.1 |
| 17 | 21.9, 24.4. |

12. The pharmaceutical composition of claim 11, wherein Taxol trihydrate III is further characterized by having δ ¹³C/ppm chemical shifts comprising:

| Carbon # | Phase III δ¹³C |
|---|---|
| 1 | 79.0 |
| 2 | 76.3 |
| 3 | 47.2, 48.2 |
| 6 | 38.4, 39.3 |
| 7 | 74.5 |
| 8 | 58.1, 58.5 |
| 10 | 76.4 |
| 11 | 133.3, 134.0 |
| 12 | 140.6, 141.0 |
| 13 | 71.6 |
| 14 | 36.4, 36.6 |
| 15 | 43.2, 43.7 |
| 16 | 26.1, 26.7 |
| 18 | 13.5, 14.5 |
| 19 | 11.6, 12.0 |

-continued

| Carbon # | Phase III δ¹³C |
|---|---|
| 20 | 77.0 |
| 21 | 169.5, 169.9 |
| 22 | 128.8, 129.0 |
| 28 | 169.9 |
| 29 | 21.6 |
| 30 | 171.1, 171.9 |
| 31 | 22.5, 22.9. |

13. A method for preparing a paclitaxel trihydrate, comprising:
preparing a starting material that includes a first crystalline paclitaxel trihydrate phase; and
inducing a first phase change in the starting material to yield a second paclitaxel trihydrate phase, wherein the second paclitaxel trihydrate phase is characterized by having δ ¹³C/ppm chemical shifts comprising:

| Carbon # | Phase II δ¹³C |
|---|---|
| 4 | 81.0 |
| 5 | 84.9 |
| 9 | 203.6, 207.4 |
| 17 | 24.0. |

14. The method of claim 13, wherein the starting material is prepared by recrystallizing paclitaxel from a water/alcohol solution, and wherein the starting material is characterized as having a ¹³C NMR spectrum illustrated at Taxol trihydrate I in FIG. 1.

15. The method of claim 13, wherein inducing the first phase change to yield the second paclitaxel trihydrate phase includes subjecting the starting material to an elevated pressure under ambient temperature and humidity conditions for a time sufficient to induce the first phase change.

16. The method of claim 15, wherein subjecting the starting material to the elevated pressure includes spinning the starting material in a solid-state NMR probe centrifuge at a rate of rotation of at least 800 Hz to 4000 Hz.

17. The method of claim 13, wherein the second paclitaxel trihydrate phase is further characterized as having a ¹³C NMR spectrum illustrated at Taxol trihydrate II in FIG. 1.

18. The method of claim 13, further comprising:
inducing a second phase change following the first phase change to yield a third paclitaxel trihydrate phase, wherein the third paclitaxel trihydrate phase is characterized by having δ ¹³C/ppm chemical shifts comprising:

| Carbon # | Phase III δ¹³C |
|---|---|
| 4 | 80.5, 81.6 |
| 5 | 84.8, 85.4 |
| 9 | 201.9, 204.1 |
| 17 | 21.9, 24.4. |

19. The method of claim 18, wherein inducing the second phase change to yield the third paclitaxel trihydrate phase includes subjecting the second paclitaxel trihydrate phase to an elevated pressure under ambient temperature and humidity conditions for a time sufficient to induce the second phase change.

20. The method of claim 19, wherein subjecting the second paclitaxel trihydrate phase to the elevated pressure includes spinning the second paclitaxel trihydrate phase in a solid-state NMR probe centrifuge at a rate of rotation of at least 800 Hz to 4000 Hz.

21. The method of claim 18, wherein the third paclitaxel trihydrate phase is further characterized as having a ¹³C NMR spectrum illustrated at Taxol trihydrate III (TA05) in FIG. 1.

* * * * *

UNITED STATES PATENT AND TRADEMARK OFFICE
CERTIFICATE OF CORRECTION

PATENT NO. : 8,633,240 B2  
APPLICATION NO. : 13/486229  
DATED : January 21, 2014  
INVENTOR(S) : Harper et al.

Page 1 of 1

It is certified that error appears in the above-identified patent and that said Letters Patent is hereby corrected as shown below:

In the Specification:

Column 1
Line 39, Insert new paragraph with heading GOVERNMENT LICENSE RIGHTS --This invention was made with government support under grant number R01 GM008521 awarded by National Institute of Health. The government has certain rights in the invention.--

Column 2
Line 25, change "opportunity, to" to --opportunity to--

Column 5
Line 67, change "or a from" to --or from--

Column 7
Line 44, change "one previously known" to --previously known--

Column 9
Line 49, change "elemental." to --elemental analysis.--

Column 11
Line 3, change "is strongly" to --are strongly--

Signed and Sealed this
Sixth Day of May, 2014

Michelle K. Lee
*Deputy Director of the United States Patent and Trademark Office*